(12) United States Patent
Carbone

(10) Patent No.: US 6,318,192 B1
(45) Date of Patent: Nov. 20, 2001

(54) OBTAINING INTERNAL SURFACE SAMPLES FROM AN IN-SERVICE PIPE

(75) Inventor: Mario J. Carbone, Bayside, NY (US)

(73) Assignee: Brooklyn Union, Brooklyn, NY (US)

( * ) Notice: Subject to any disclaimer, the term of this patent is extended or adjusted under 35 U.S.C. 154(b) by 0 days.

(21) Appl. No.: 09/175,325

(22) Filed: Oct. 20, 1998

(51) Int. Cl.⁷ .................. G01N 1/08; G01N 1/12
(52) U.S. Cl. .................... 73/863.81; 73/864.71
(58) Field of Search ............ 73/863.81, 864.71

(56) References Cited

U.S. PATENT DOCUMENTS

| | | |
|---|---|---|
| 1,636,243 | 7/1927 | Rasmussen . |
| 3,842,864 | 10/1974 | Riegel et al. ............. 138/93 |
| 3,910,298 | 10/1975 | Shotmeyer ............. 137/1 |
| 4,235,244 * | 11/1980 | Abele et al. ............ 73/864.71 X |
| 4,888,154 * | 12/1989 | Sheridan ............. 73/863.81 X |
| 4,919,892 | 4/1990 | Plumb ............. 422/58 |
| 5,029,484 * | 7/1991 | Somers et al. ............. 73/863.81 |
| 5,269,968 | 12/1993 | Miller et al. ............. 252/351 |
| 5,400,826 | 3/1995 | Clough ............. 138/89 |
| 5,463,908 | 11/1995 | Rosolia ............. 73/863.83 |
| 5,531,130 | 7/1996 | Welker ............. 73/863.81 |
| 5,686,674 | 11/1997 | Lowry et al. ............. 73/865.8 |
| 5,823,592 * | 10/1998 | Kalindindi ............. 73/864.71 X |
| 5,859,375 * | 1/1999 | Danylewych-May et al. ... 73/864.71 |
| 6,021,681 * | 2/2000 | Jezck ............. 73/864.71 |

FOREIGN PATENT DOCUMENTS

| | | | |
|---|---|---|---|
| 137939 * | 11/1952 | (CH) | 73/863.81 |
| 461952 * | 2/1975 | (SU) | 73/863.81 |

* cited by examiner

Primary Examiner—Thomas P. Noland
(74) Attorney, Agent, or Firm—Fitzpatrick, Cella, Harper & Scinto

(57) ABSTRACT

Samples of contaminants are obtained from the interior surface of a pipe main by inserting, through an opening in the pipe main, an inflatable pillow bag or balloon-like element in deflated and collapsed condition, and having a swab affixed to its outer surface. The balloon-like element is inflated inside the pipe main to extend the swab to a generally planar configuration and to press it against the inner surface of the pipe main so that it absorbs contaminants from the surface. The balloon-like element, with the swab attached, is then deflated and recollapsed; and together with the swab, is withdrawn from the pipe main.

6 Claims, 5 Drawing Sheets

OBTAINING INTERNAL SURFACE SAMPLES FROM AN IN-SERVICE PIPE

BACKGROUND OF THE INVENTION

1. Field of the Invention

This invention relates to the obtaining of contaminant samples which have been deposited along the interior surface of a pipe; and more particularly it concerns a novel method and apparatus for applying a large area swab to the inner surface of a pipe so that a representative sample of the contaminant can be recovered from the pipe without interfering with the flow of fluid through the pipe.

2. Description of the Related Art

Large diameter pipes, such as gas mains, are often required to convey gasses which may contain harmful contaminants such as polychlorinated biphenyls (PCBs) or Benzine. These contaminants may precipitate out of the gas stream and become deposited along the interior service of the pipe. Thereafter, when clean gas passes through the pipe, it comes into contact with the contaminant deposits so that it may also become contaminated.

It is therefore important, at any given time, to know whether sufficient contaminants have become deposited long the inner surface of a pipe such that they would be likely to cause further contamination of clean gas passing through the pipe. It is also important not to interrupt gas flow through the pipe or otherwise disrupt its operation while inspecting its inner surface for contaminants. This becomes a difficult problem in that in order to obtain an accurate indication of the condition of a pipe's inner surface, a minimum area of the surface, usually at least four square inches (25 square centimeters), must be examined; and to expose this much of a pipe's interior while maintaining normal gas flow through the pipe is especially difficult.

U.S. Pat. No. 5,269,968 discloses a technique for removing PCBs from the contaminated inner surface of a pipe by means of a swab sampling technique in which the pipe is first cut into pieces to expose its inner surfaces.

U.S. Pat. No. 5,686,674 discloses the use of a sensor which is dragged through the interior of a pipe to sense radioactive contamination along the inner surface of the pipe.

U.S. Pat. No. 4,919,892 discloses the use of a perforated housing which is positioned in the path of fluid flow in a pipe to absorb contaminants from the fluid passing through the pipe.

U.S. Pat. Nos. 5,463,908 and No. 5,531,130 relate to the use of probes which are inserted into pipes to measure conditions in the fluids which flow through the pipes.

U.S. Pat. Nos. 3,842,864, 3,910,298 and 5,400,826 show the use of inflatable balloons inside of pipes to stop the flow of fluid in the pipe.

U.S. Pat. No. 1,636,243 shows the use of an inflatable balloon to press a pad against the interior of a pipe joint to prevent sealant, which is being applied to the exterior of the pipe joint, from leaking into the pipe.

A satisfactory method or means for effectively ascertaining the contamination of an inner pipe surface while fluids are flowing normally through it appears not to be disclosed in the prior art.

SUMMARY OF THE INVENTION

The present invention, in one aspect, provides an novel method of obtaining surface samples from the inner surface of a pipe main through which a fluid is flowing. According to this novel method, an opening is provided in the pipe main. There is also provided an inflatable balloon-like element with a swab affixed to its outer surface. The balloon-like element is inserted, in deflated and collapsed condition and with the swab affixed thereto, through the opening in the pipe main and into the interior of the pipe main. Then the balloon-like element is caused to inflate and expand inside the pipe main to extend the swab into a generally planar configuration and to press the swab against an inner surface of the pipe main. Thereafter, the balloon-like element is deflated and collapsed; and the collapsed balloon-like element with the swab attached, is removed from the interior of the pipe main.

In another aspect the invention involves a novel apparatus for use in obtaining samples of contaminants from the inner surface of a pipe main. This novel apparatus comprises a first pipe which is constructed and arranged to be connected to a pipe main so that one end of the first pipe opens into the interior of the pipe main while its other end extends outside of the pipe main. There is also provided a second pipe having attached at one end thereof, a balloon-like element made of a flexible material and which can be inflated by application of fluid pressure through the second pipe. A swab is attached to the balloon-like element so that when the balloon-like element is inflated, the swab extends generally in a plane. When the balloon-like element is deflated, it collapses, together with the swab; and in this condition the balloon-like element and the swab may be pushed by means of the second pipe, through the first pipe and into the interior of a pipe main. Means are provided for applying fluid pressure through the second pipe to inflate the balloon-like element inside the pipe main so that it presses said swab against the interior surface of the pipe main, whereby material from the interior surface adheres to said the swab. Means are provided for thereafter releasing the fluid pressure to deflate and collapse the balloon-like element and the swab so that they can be withdrawn together from the interior of the pipe main through the first pipe.

DETAILED DESCRIPTION OF THE PREFERRED EMBODIMENT

Figure 1:
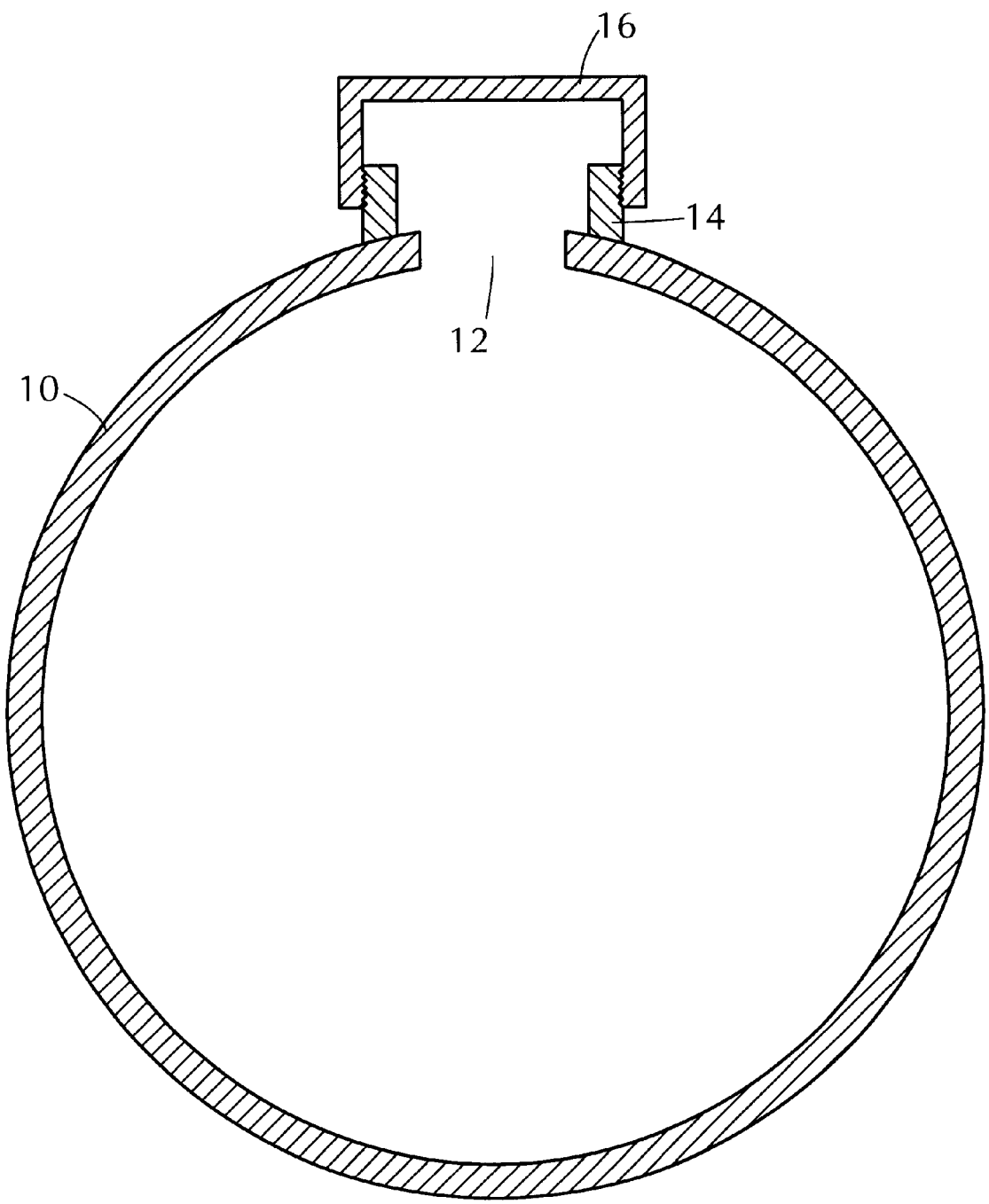
FIG. 1 is a cross-sectional view of a pipe main from the interior surface of which a contaminant sample may be obtained according to the present invention.

As shown in FIG. 1 a gas pipe main 10 (shown in cross-section) is provided with an opening 12 at its upper portion. This opening 12 is surrounded by a threaded nipple 14 which is welded to the exterior of the pipe main. A cap 16 is threaded onto the nipple 14 to prevent escape of gas from the interior of the pipe main while allowing convenient access to the opening 12. The pipe main may be constructed in this fashion when it is installed. Alternatively, the opening 12 may be drilled and the nipple 14 installed at any later time, as when there is a suspicion of contaminants on the inner surface of the pipe main.

Figure 2:
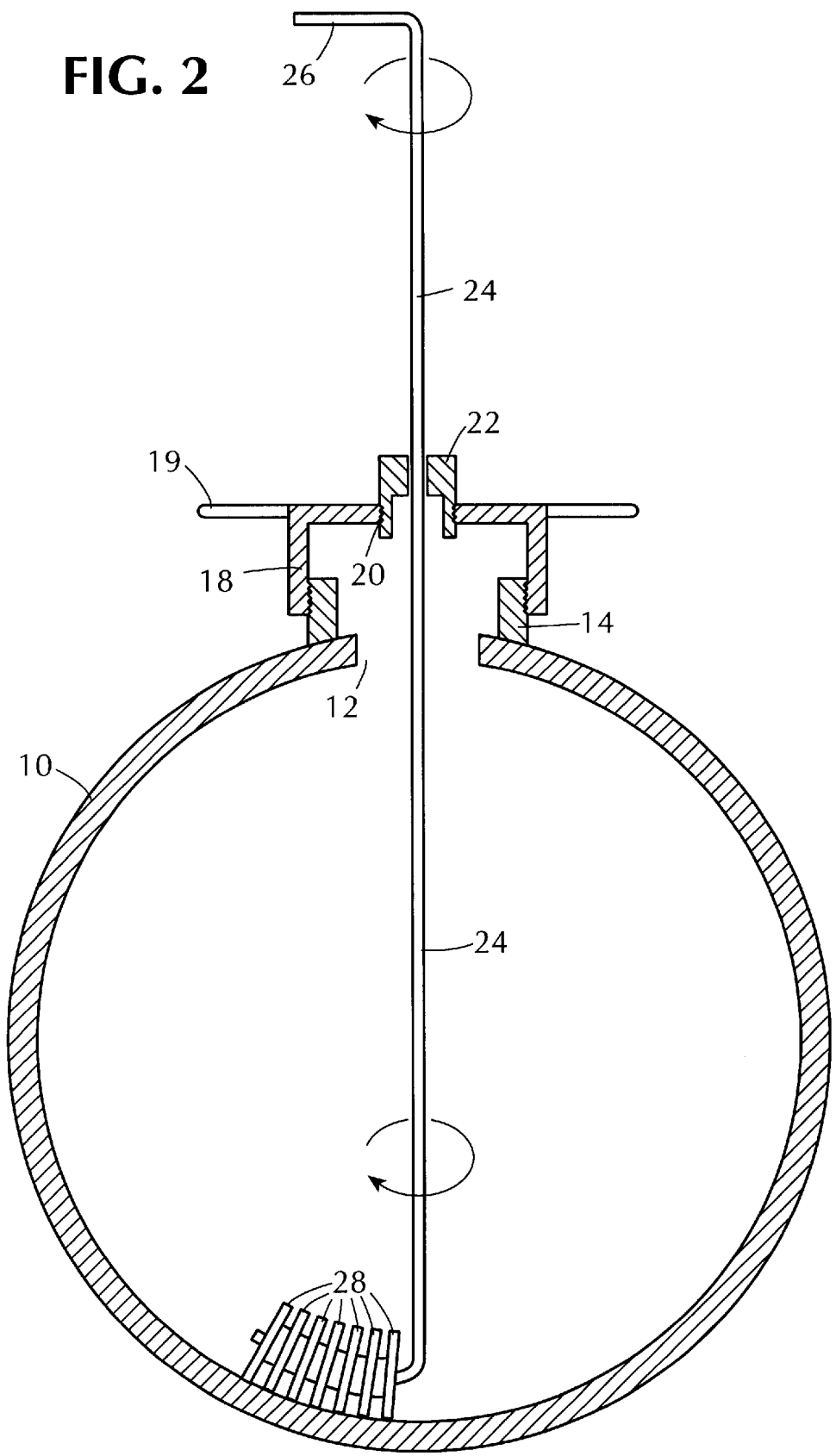
FIG. 2 is a view similar to FIG. 1 but showing a precleaning tool applied to the interior of the pipe main.

FIG. 2 shows an arrangement for precleaning the inner surface of the pipe main 10 to remove non-chemical contaminants, such as iron cuttings, which may have been formed and dropped inside the pipe main upon drilling the opening 12. As shown in FIG. 2, the cap 16 is replaced by a precleaning adapter 18 which is threaded onto the nipple 14. The adapter 18 has handles 19 for tightening it onto the nipple 14. The precleaning adapter 18 has a central opening 20; and a bushing assembly 22 is threaded into the central opening.

An elongated cleaning rod 24 extends through the bushing assembly 22 and is moveable up and down and rotationally in the assembly without significant loss of gas from inside the pipe main 10. The upper end of the rod 24 is bent to form a handle 26 for manipulating it during a precleaning operation.

The lower end of the cleaning rod 24, which is inside the pipe main 10, is flexible and has several magnets 28 mounted thereon.

As shown in FIG. 2 the interior of the pipe main 10 is cleaned from magnetic objects, such as cuttings, by manipulating the rod 24 so that its lower end flexes and the magnets 28 are caused to slide over the inner surface of the main 10. The magnets 28 cause the magnetic objects to adhere thereto so that they can be removed from the pipe main 10 by removing the precleaning adapter 18 and pulling the rod 24 and the magnets 28 out from the opening 12 in the pipe main 10.

Figure 3:
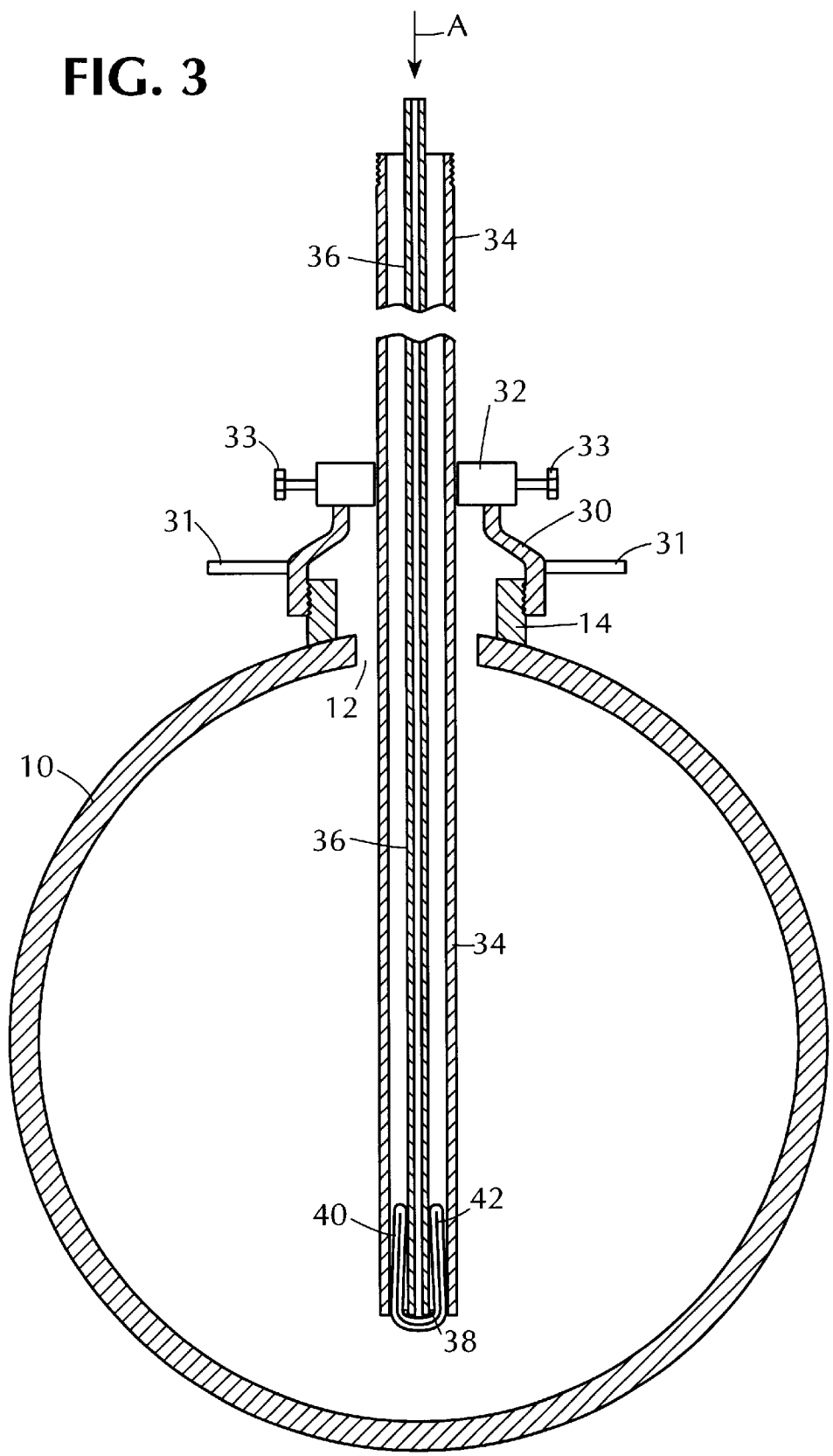
FIG. 3 is a view similar to FIG. 2 but showing the insertion of a sampling swab into the interior of the pipe main.

FIG. 3 shows arrangements according to the present invention for obtaining a sampling of contaminants, such as PCBs or benzine, which may have become deposited on the inner surface of the pipe main 10. As shown, there is provided a sampling adapter 30 which is threaded onto the nipple 14. The adapter 30 also has handles 31, which may be used to tighten the adapter onto the nipple. The sampling adapter 30 is tapered inwardly above the nipple 14 and has a gas lock collar 32 at the upper end thereof. The gas lock collar 32 allows a pipe to be inserted into the sampling adapter 30 without leakage of gas from the pipe main 10.

An elongated first pipe 34 is inserted into the gas lock collar 32 in the sampling adapter 30 so that the lower end of the first pipe opens into the interior of the pipe main 10. The first pipe is held to the collar 32 by means of setscrew bolts 33. The first pipe 34 extends up from the pipe main 10 by any desired distance. For example, if the pipe main 10 is buried in the ground at a particular depth, the first pipe 34 should be long enough to extend up out of the ground.

An elongated second pipe 36, of smaller diameter than the first pipe 34, is inserted into the upper end of the first pipe and is moved down through the first pipe as indicated by the arrow A in FIG. 3. As shown, the second pipe 36 extends through the first pipe 34 and into interior of the pipe main 10.

At the lower end of the second pipe 36, there is provided a pinch clamp 38 to which is attached an inflatable pillow air bag or balloon-like element 40. In FIG. 3, the pillow air bag or balloon 40 is shown deflated and collapsed, in which condition it can be pushed down through the first pipe 34 until it exits into the interior of the pipe main 10 below the first pipe 34. The pillow or air bag balloon-like element 40 has a swab 42 attached to its bottom surface. The swab 42 is also in collapsed condition and is pushed down through the first pipe 34 with the pillow air bag 40.

Figure 4:
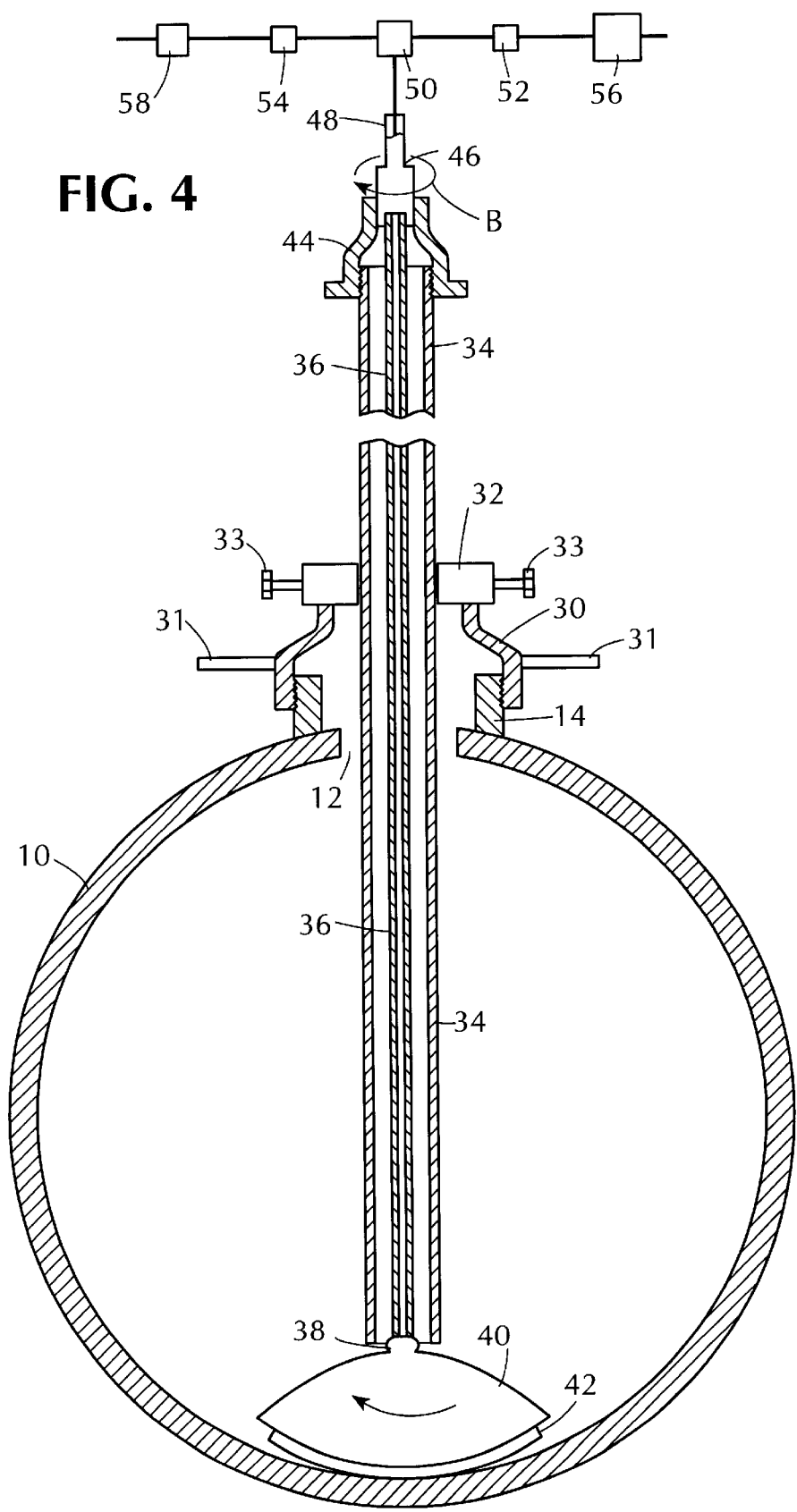
FIG. 4 is a view similar to FIG. 3 but showing the extension of the sampling swab by means of a balloon-like element inside the pipe main.

As shown in FIG. 4, a bell reducer 44 is threaded onto the upper end of the first pipe 34. The bell reducer 44 has a smaller diameter central opening 38 into which a fitting 46 extends. The fitting is connected to the upper end of the second pipe 36 and to an air line 48 to supply pressurized air down through the second pipe 36. A T-connector 50 is connected to the air line 48. The T-connector has two branches which are connected, respectively, to quick-connect fittings 52 and 54. The first quick-connect fitting 48 is connected to an air pump 56, which may, for example, be an ordinary bicycle tire pump; and the second quick-disconnect fitting 54 is connected to a pressure release valve 58.

The second pipe 36 is lowered through the first pipe 34 so that the pillow air bag or balloon 40 exits through the lower end of the first pipe. The pressure release valve 58 is closed and the air pump 56 is then operated to force pressurized air through the T-connector 50, the air line 48 and the fitting 46 into the second pipe 36 and down into the pillow air bag 49. This inflates the pillow air bag 40 and expands it to the condition shown in FIG. 4. This expansion causes the swab 42 to extend to a generally planar configuration so that its entire surface area faces the internal surface of the pipe main 10. By positioning the second pipe near the surface of the pipe main 10, the expansion of the pillow air bag 40 by the pressure applied through the second pipe 36 causes the full surface area of the swab 42 to be pressed against the inner surface of the pipe main so that it will absorb a proper amount of contaminants from the pipe main inner surface.

The opening 12 in the pipe main 10 in the illustrated example is two inches (5.08 cm) in diameter but the swab 42, when fully extended by inflation of the pillow air bag 40 may be four inches (10.16 cm) square so as to obtain a sufficient sample from the pipe main surface. The swab 42 may be attached to the pillow air bag 40 by any convenient means which will hold it securely to the pillow air bag and yet allow ready detachment. Some of the means for holding the swab to the air bag could include snap fasteners, barb and hook material such as Velcro®, zippers or even stitching.

The pillow air bag 40 does not necessarily have to have the identical contour of the pipe main inner surface. The pressure inside the pillow air bag needs only to be high enough to expand it and extend the swab 42. The pillow air bag, however, when inflated may be pressed against the inner wall of the pipe main 10; and, because of its flexibility, it and the swab will conform to contour of the pipe main inner surface.

In order to be certain that the swab 42 has obtained a full sample, the second pipe 36 may be rotated at its upper end as indicated by the Arrow B so as to cause the swab to rub against the inner surface of the pipe main 10, as shown in FIG. 4. This ensures a good recovery of any contaminants that may be present on the pipe main inner surface.

Figure 5:
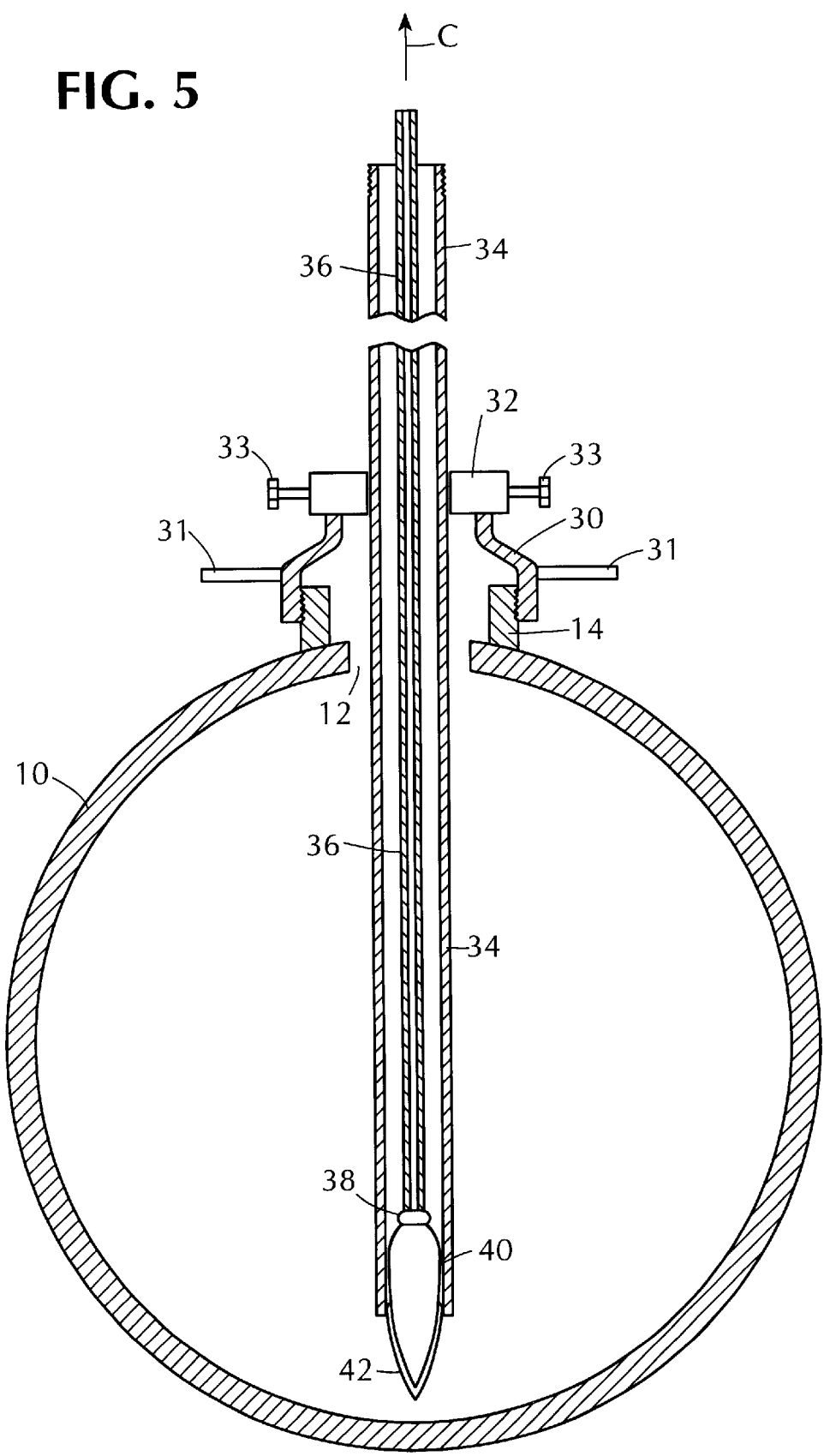
FIG. 5 is a view similar to FIG. 4 but showing the removal of the sampling swab from the interior of the pipe main.

When the contaminant sample has been absorbed onto the swab 42, the pressure release valve 58 is opened and the pillow air bag or balloon-like element 40 is deflated and collapsed along with the swab 42, as shown in FIG. 5. Then the second pipe 36 may be pulled up to draw the collapsed pillow air bag 40 and swab 42 up through the first pipe 34 as indicated by the arrow C in FIG. 5. In order to recover the swab, the bell reducer 44 is unscrewed from the upper end of the first pipe 34 so that the pillow air bag and swab may be removed through the upper end of the first pipe 40. The swab may then be detached from the pillow air bag and submitted to testing to determine the nature and quantity of the contaminant. A new swab may then be attached to the pillow air bag 40 to obtain a subsequent contaminant sample. Also, if a different size pillow air bag is desired for removal of a contaminant sample from a different size pipe main, the pinch clamp 38 may be released and the pillow air bag 40 may be removed and replaced by a new pillow air bag at the bottom end of the second pipe 36.

When all required samples have been obtained, the sampling adapter 30 may be removed from the nipple 14 on the pipe main 10 and replaced by the cap 16.

It will be appreciated that with this invention, it is possible to obtain a representative sample of a contaminant from the inner surface of a pipe by means of a swab which has an extensive surface area, even though there is only a small opening in the pipe through which the web may be inserted.

What is claimed is:

1. Apparatus for obtaining a sample deposit from the interior surface of a pipe main through which a fluid medium flows, said apparatus comprising:

a first pipe constructed and arranged to be connected to a pipe main so that one end of the first pipe opens into the interior of the pipe main while its other end extends outside of the pipe main;

a second, fluid pressure supply pipe having attached at one end thereof a balloon-like element made of a flexible material and which can be inflated by application of fluid pressure through said second pipe;

a swab attached to said balloon-like element so that when said balloon is inflated said swab extends generally in a plan, said balloon, when deflated and with the swab attached, being insertable together with said second pipe, through the first pipe and into the interior of a pipe main, means for applying fluid pressure through said second pipe to inflate said balloon-like element inside said pipe main so that it presses said swab against the interior surface of the pipe main whereby material from said interior surface adheres to said the swab;

means for thereafter releasing the fluid pressure to deflate and collapse the ballon-like element and the swab so that they can be withdrawn from the interior of the pipe main through the first pipe.

2. Apparatus according to claim 1 wherein said swab is detachable from said balloon-like element.

3. Apparatus according to claim 1 wherein said swab is at least 4" square.

4. Apparatus according to claim 1 wherein said balloon-like element is a rubberized fabric material.

5. Apparatus according to claim 1 wherein said balloon-like element is held to said one end of said second pipe by means of a pinch clamp.

6. Apparatus according to claim 1 wherein said second pipe is rotatable in said first pipe while said balloon-like element is inflated so as to cause said swab to rub against the pipe main interior surface.

\* \* \* \* \*

UNITED STATES PATENT AND TRADEMARK OFFICE
CERTIFICATE OF CORRECTION

PATENT NO. : 6,318,192 B1
DATED : November 20, 2001
INVENTOR(S) : Mario J. Carbone Page 1 of 1

It is certified that error appears in the above-identified patent and that said Letters Patent is hereby corrected as shown below:

<u>Column 1,</u>
Line 25, "long" should read -- along --; and
Line 49, "Nos. 5,463,908" should read -- No. 5,463,908 --; and
Line 66, "an" should read -- a --.

Signed and Sealed this

Twenty-first Day of May, 2002

Attest:

JAMES E. ROGAN
*Director of the United States Patent and Trademark Office*

*Attesting Officer*